United States Patent [19]

Buchanan

[11] Patent Number: 5,205,281

[45] Date of Patent: Apr. 27, 1993

[54] ORAL AIRWAY WITH OXIMETRY MEANS

[76] Inventor: Dale C. Buchanan, 4217 Horeshoe Bend, Matthews, N.C. 28105

[21] Appl. No.: 739,881

[22] Filed: Aug. 2, 1991

[51] Int. Cl.$^5$ .................... A61M 16/00; A62B 9/06; A61B 6/00; A61B 5/00
[52] U.S. Cl. ...................... 128/207.14; 128/205.23; 128/204.23; 128/633; 128/664
[58] Field of Search .................. 128/716, 207.14, 630, 128/634, 644, 204.23, 205.23, 633, 637, 664

[56] References Cited

U.S. PATENT DOCUMENTS

| | | | |
|---|---|---|---|
| 4,231,364 | 11/1980 | Speshyock | 128/207.14 |
| 4,564,021 | 1/1986 | Siegmann et al. | 128/716 |
| 4,640,293 | 2/1987 | Garbe | 128/716 |
| 4,651,746 | 3/1987 | Wall | 128/716 |
| 4,676,240 | 6/1987 | Gardy | 128/207.14 |
| 4,850,371 | 7/1989 | Broadhurst et al. | 128/207.14 |
| 4,928,691 | 5/1990 | Nicolson et al. | |
| 5,005,573 | 4/1991 | Buchanan . | |

FOREIGN PATENT DOCUMENTS 2126719 3/1984 United Kingdom .............. 128/716

OTHER PUBLICATIONS

"Optical Fluorescence . . . Blood Gas Monitoring System", Gehrich et al, IEEE Trans. on Biomed. Egr, vol. BME-33, No. 2, Feb. 1986.
"A Buccal Sensor for Measuring Arterial Oxygen Saturation" *Letters to the Editor,* Joel B. Gunter. M.D., pp. 417–418.
David R. Jobes et al "Monitoring of Arterial Hemoglobin Oxygen Saturation Using a Tongue Sensor" *Clinical Reports,* pp. 186–188.
"Oral Impulse Oximetry in Small Children" *Letters to the Editor,* Guillermon E. Lema, M.D. p. 414.

*Primary Examiner*—Edgar S. Burr
*Assistant Examiner*—K. L. Asher
*Attorney, Agent, or Firm*—Shefte, Pinckney & Sawyer

[57] ABSTRACT

The present invention discloses an oral airway for insertion within a surgical patient's mouth and over the patient's tongue for preventing blockage of the pharynx during surgical and like procedures. According to the present invention, the airway is provided with an arrangement for transmitting light through the patient's tongue from a point on the oral airway bearing a transmitting device to a point on the oral airway bearing a detecting device. The transmitting devices and detecting devices are positioned in a spaced-apart relation on the oral airway so that the light transmitted from the transmitting device passes through at least a portion of the patient's tongue before being received by the detecting device. Additionally, an operative connecting device is provided for connecting the transmitting device and detecting device with an oximeter for measuring saturation of the patient's blood as a function of the transmitted light received by the detecting device.

7 Claims, 3 Drawing Sheets

ORAL AIRWAY WITH OXIMETRY MEANS

FIELD OF THE INVENTION

The present invention relates broadly to surgical appliances and, more particularly, to oximetry devices for determining oxygen saturation in a surgery patient's blood.

BACKGROUND OF THE INVENTION

In recent years, the measurement of blood oxygen saturation, commonly referred to as oximetry, has come into increasingly widespread use during surgical procedures as a means for monitoring and preventing undetected hypoxemia of the surgical patient. Essentially, oximetry measures the amount of oxygenated hemoglobin in the blood of the patient as a percentage of the total hemoglobin in the blood. Various devices, typically referred to as oximeters, are available for performing oximetry measurements.

So-called non-invasive pulse oximeters are configured to attach to a patient's fingertip, ear lobe, or nose and are operable to transmit light of different wavelengths or colors, typically in the red and infrared spectrums, into the body part and to detect the light transmitted therethrough or the light reflected thereby. It is known that the ability of blood hemoglobin to absorb light varies in relation to the level of oxygenation of the hemoglobin. Accordingly, detection of the reflected or transmitted light from a pulse oximeter indicates the amount of the light absorbed from which the blood oxygen saturation can be calculated.

While the non-invasive pulse oximeters of the aforementioned type provide substantial advantages over previous oximetry methods, which required the withdrawal of blood samples from a patient, pulse oximeters are still subject to several disadvantages. First, since existing oximeters are typically attached to peripheral areas of the patient's body, when the patient is in the state of low blood profusion, e.g., when the patient has lost a substantial amount of blood, is cold, or has peripheral vascular disease, or for other reasons has poor blood circulation, difficulty may often be experienced in obtaining a sufficient light transmission or reflectance signal from which to calculate the patient's blood oxygen saturation. This is particularly so in cases of shock or hypothermia or other conditions of lowered or inconsistent circulation. Likewise, the ambient light sources and relative movement of the patient and the oximeter may also interfere with the accuracy of the measurements and calculations obtained.

One type of oximetry device employing such non-invasive methods is disclosed in U.S. Pat. No. 4,928,691 which issued on May 29, 1990 to Nicolson et al. This device is a rigid but malleable sensor probe which may be attached to the tongue and has a light source and sensor attached thereto for transmitting light through the tongue tissue to obtain blood oxygen saturation measurements.

As with the device described in the '691 patent, one problem with previous oximetry devices is the fact that the oximetry device is an additional device needed during the surgical or other procedure. The addition of such devices during the surgical procedure increases both the expense and complexity of any surgical procedure. U.S. Pat. No. 5,005,573 to Applicant and issued on Apr. 9, 1991 discloses an endotracheal breathing tube for use in surgical operations which is equipped with a light emitting device adjacent its distal end to reside within the patient's trachea during use and with a compatible photosensitive detector positionable outside the patient's body in contact with the neck to intercept the light transmitted from the light emitting device for performing accurate oximetry measurements and calculations of the patient's blood oxygen saturation.

While the device disclosed in the '573 patent does eliminate the need for a separate oximetry device, it still requires the surgeon or assistant to position the light receiving or detecting device securely on the patient and may still fail to make a reading should the device on the patient's neck be shifted accidentally. It would therefore be beneficial to provide for an oximetry device which is a part of a device already used as surgery, which does not require the attention of medical personnel to accomplish the positioning of the light transmitting or light receiving device, and which yields precise oxygen saturation readings for those patients whose lowered or inconsistent circulation produces inaccurate readings in sensors located at peripheral sites.

SUMMARY OF THE INVENTION

It is accordingly an object of the present invention to provide a device which enables oximetry measurements and calculations to be performed during surgical procedures with improved accuracy over conventional non-invasive pulse oximeters. It is a particular object of the present invention to incorporate such an oximetry device in an oral airway to enable more simple, accurate and quickly responsive oximetry measurements to be made through the patient's tongue while also simultaneously enabling continual prevention of the patient's tongue from blocking air passage through the pharynx.

Briefly summarized, the present invention provides for an oral airway for insertion within a surgical patient's mouth and over the patient's tongue for preventing blockage of the pharynx during surgical and like procedures. During surgery under general anesthesia, it is standard practice to insert an oral airway into the patient's mouth and over the patient's tongue. Under general anesthesia, the patient's tongue typically curves upwards and conforms to the underside of the oral airway. Such an oral airway assists in maintaining the patient's breathing by preventing the patient's tongue from blocking the pharynx.

According to the present invention, the airway is provided with an arrangement for transmitting light through the patient's tongue from a point on the oral airway bearing a transmitting device to a point on the oral airway bearing a detecting device. The transmitting devices and detecting devices are positioned in a spaced-apart relation on the body of the oral airway so that the light transmitted from the transmitting device passes through at least a portion of the patient's tongue before being received by the detecting device. Additionally, an operative connecting device is provided for connecting the transmitting device and detecting device with an oximeter for measuring oxygen saturation of the patient's blood as a function of the transmitted light received by the detecting device.

In one embodiment of the present invention, the transmitting arrangement includes a light emitting device, such as a light emitting diode, affixed to the oral airway. Appropriate electrical wiring operatively connects the light emitting device to the detecting device.

In an alternate embodiment, the light emitting device is operatively connected to an optical fiber which extends along the oral airway to a light emitting terminus of the fiber at the location of the transmitting device.

The detecting arrangement preferably includes a photosensitive device, such a photodiode. The photo sensitive device is operatively connected to the oximeter by suitable electrical wiring.

DESCRIPTION OF THE PREFERRED EMBODIMENT

Figure 1:
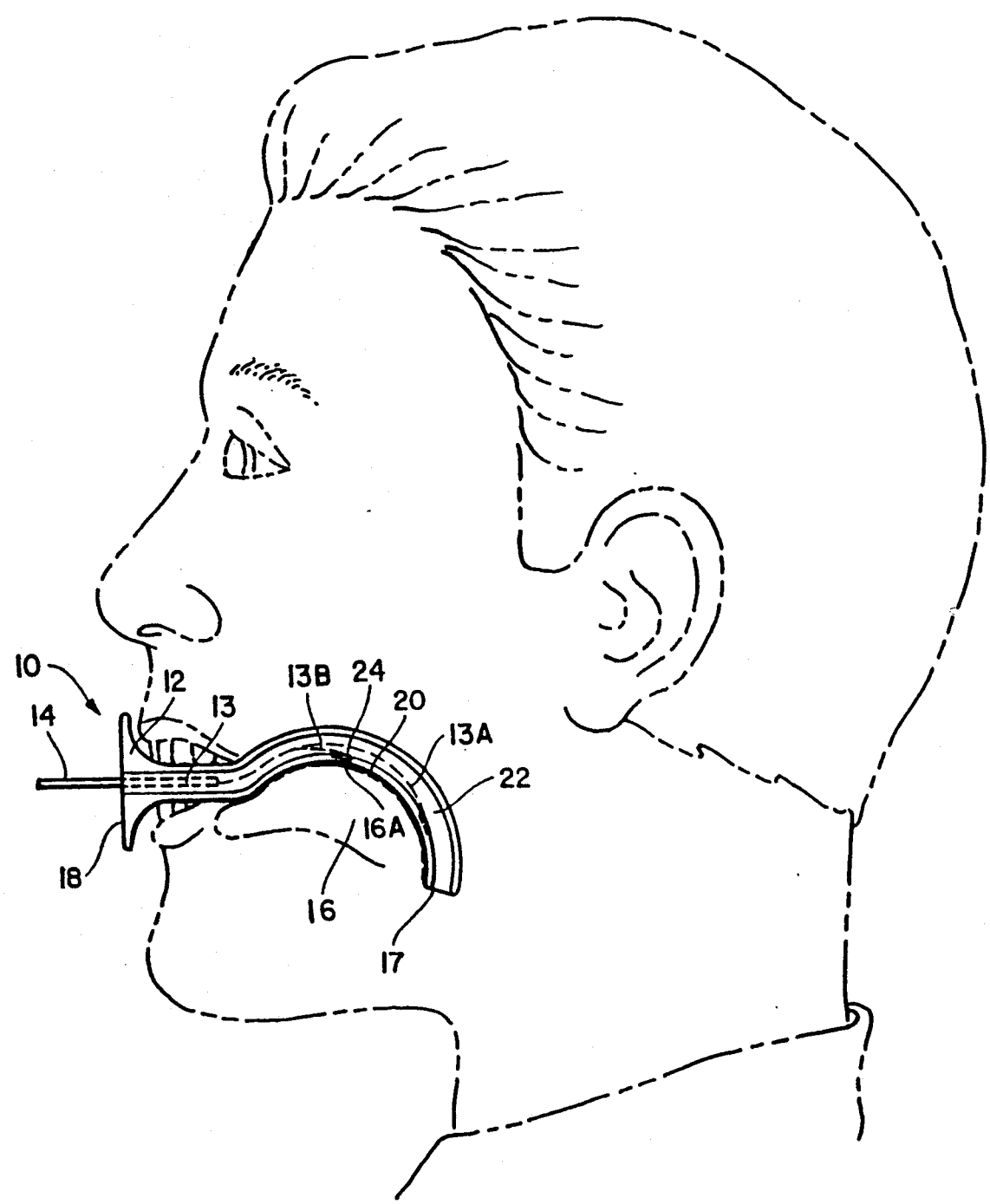
FIG. 1 is a schematic side elevational view of an oral airway according to one preferred embodiment of the present invention.

Referring now to the accompanying drawings and initially to FIG. 1, an oral airway according to a preferred embodiment of the present invention is generally indicated in a patient's mouth at 10. Basically, the oral airway 10 includes an airway body 12 to which an oximetry measuring device 14 is affixed via a cable or other suitable oximetry connecting means 13. The airway 10 is placed into a patient's mouth and over the patient's tongue, generally shown at 16, during surgery or other like procedures.

The airway body 12 may be of any conventional oral airway construction, the airway body 12 illustrated in FIG. 1 being schematically representative of one common type of oral airway.

Figure 2:
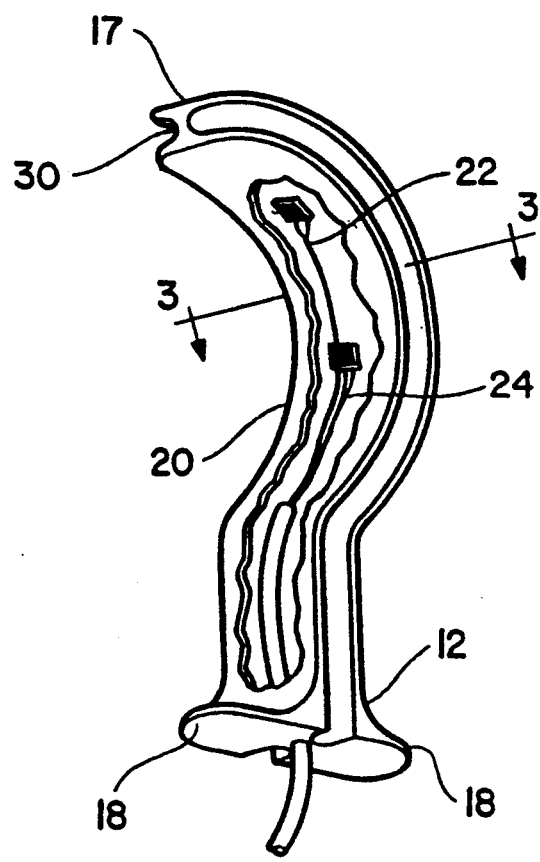
FIG. 2 is a perspective view of the device shown in FIG. 1.

As seen in FIG. 2, the airway body 12 is I-shaped in cross section along its entire length and has an end flange 18 at the terminating end of the airway. The terminating end containing the flange end 18 is the portion of the airway closest to the mouth of the patient during use.

In use, the leading end 17 of the airway body 12 is inserted into the patient's mouth and over the patient's tongue with the terminating end bearing end flanges 18 resting against the patient's teeth so that flange 18 may be in front of the lips or the teeth. During surgical procedures, the patient's tongue typically curves as is shown in FIG. 1 in area 16A so that the tongue conforms to the curved area 20 of the airway 10.

Transmitting device 22 and detecting device 24 are positioned in spaced-apart relation in the curved area 20 of airway 10. The transmitting and detecting devices 22 and 24 are spaced apart so that when the transmitting device 22 transmits light in the direction of the detecting device 24, the transmission line 26 crosses through the substance 16A of tongue 16.

Transmitting device 22 and receiving device 24 are electrically connected to each other and the oximeter 14 via electrical connection means 13 through branches 13A and 13B. The electrical connection means may be optical fibers.

Figure 3:
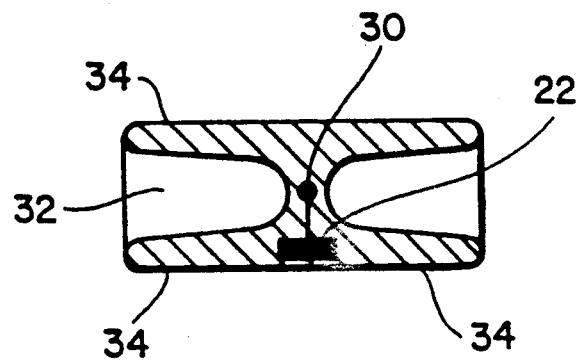
FIG. 3 is a cross section of a preferred embodiment of the present invention along line 3—3 of FIG. 2.
Figure 4:
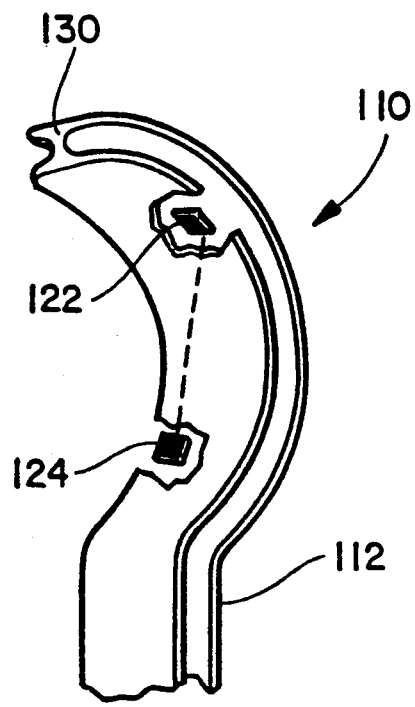
FIG. 4 is another perspective view of an oral airway illustrating yet another preferred embodiment of the present invention.
Figure 5:
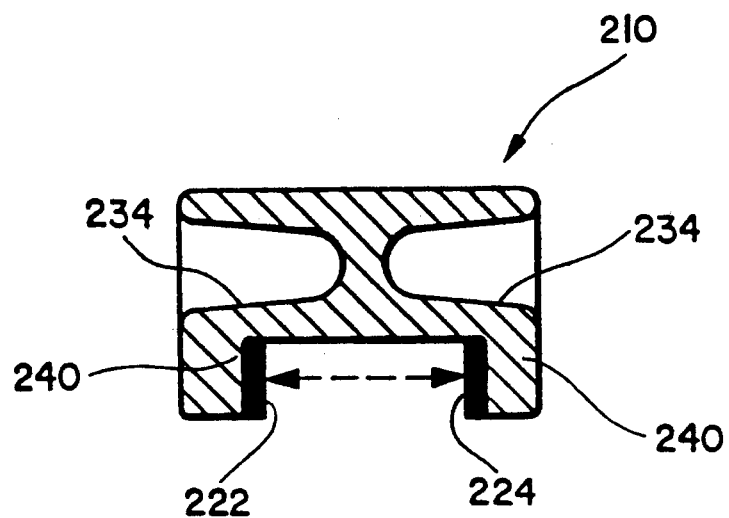
FIG. 5 is a cross section of an oral airway according to still another preferred embodiment of the present invention.

The transmitting and detecting devices 22 and 24 may be positioned within airway 10 as shown in FIG. 3 by being embedded in the central area 30 of the airway body 12. FIG. 3 shows the transmitting device 22 as well as the branch of the electrical connection means 13A embedded in the central area 30 of airway 10. Alternatively, the transmitting and detecting devices may be embedded in or secured to the side flanges 34 of the airway as seen in FIGS. 4 and 5, as more fully described hereinafter.

In operation, the transmitting device 22 is preferably a light emitting device such as a light emitting diode and is operatively controlled by the oximeter 14 to emit light in a direction linearly outwardly from the curved portion 20 of the airway 10. Detecting device 24 which is preferably a photodiode is adapted to receive and detect the light transmitted by the light emitting diode 22 when the photodiode or photodiodes 24 are positioned within the path of the transmitted light. The light emitting diodes 22 and photodiodes 24 are fixed within the airway 10 to insure accurate transmission and detection of the light. Thus, movement of the patient or an accidental touching of the airway 10 still results in accurate detection of blood oxygen saturation.

Alternatively, electrical connection means 13A and/or 13B may be optical fibers with the light emitting terminus of fiber 13A constituting transmitting device 22 via a light emitting device operatively connected to the optical fiber for directing light to travel along the fiber to the terminus.

Thus, upon initial insertion of the airway body 12 into the mouth of a surgical patient, the light emitting diode or diodes 22 and the photodiode o diodes 24 enable the surgeons and assistants to prevent the tongue from blocking the trachea while simultaneously allowing the oximeter 14 to compare the amount or intensity of light detected by the photodiode or diodes 24 with the amount of intensity of light transmitted by the light emitting diode or diodes 22 and to obtain thereby a measurement of the amount of light absorbed by the hemoglobin in the blood passing through the intervening blood vessels in the patient's tongue. In conventional fashion, the oximetry device 14 controls the light emitting diode or diodes 22 to transmit both red and infrared light in performing such measurements and from such measurements, calculates the level of blood oxygen saturation for the patient.

Referring now to FIG. 4, an alternative embodiment of the oral airway of the present invention is indicated generally at 110 and basically includes a body 112 identical to that of the embodiment of FIGS. 1 and 2 with an alternative positioning of transmitting and detecting devices 122,124. In this embodiment, the transmitting 122 and detecting 124 devices are not positioned within the central area as in FIG. 3, but rather, are positioned with one device on either side of the central area 130 on the side flanges in a spaced-apart relation. This embodiment has the advantage of optimizing the signal strength of the light transmitted by transmitting device 122.

Yet another embodiment of the present invention is shown in FIG. 5 where the oral airway 210 of the present invention includes a body 212 identical to the embodiment of FIGS. 1–4 except that lower side flanges 234 bear appendages 240. In this embodiment, the appendages 240 carry the transmitting device 222 and the detecting device 224 such that the light pathway is through the portion of the patient's tongue situated along the short axis of the oral airway 210.

In summary, an oral airway for use in surgical operations is equipped with a light emitting device and a light detecting device which when used comes in contact with the patient's tongue so that a light pathway is formed through a portion of the patient's tongue, which allows for the performing of accurate oximetry measurements and calculations of the patient's blood oxygen saturation.

It will therefore be readily understood by those persons skilled in the art that the present invention is susceptible of broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. An oral airway for insertion over a surgical patient's tongue, which both assists in patient breathing and provides for the measurement of oxygen saturation in the patient's blood, comprising:

a) a main body configured to extend through the patient's mouth over the tongue to prevent blockage of the patient's pharnyx during surgery;
   b) means for transmitting light;
   c) means for detecting light transmitted by said transmitting means;
   d) said transmitting means and said detecting means being positioned on said main body in spaced relation to one another for passage of light through the patient's tongue when transmitted from said transmitting means to said detecting means during surgical use of the airway; and
   e) means for operatively connecting said transmitting means and said detecting means with an oximeter for measuring oxygen saturation in the patient's blood as a function of the transmitted light detected by said detecting means.

2. The oral airway of claim 1 further characterized in that said transmitting means comprises a light emitting device affixed to the airway.

3. The oral airway of claim 2 further characterized in that said oximeter connecting means comprises electrical wiring means extending along the airway from said detecting means to said light emitting device.

4. The oral airway of claim 2 wherein said light emitting device comprises a light emitting diode.

5. The oral airway of claim I further characterized in that said detecting means comprises a photosensitive device.

6. The oral airway of claim 1 characterized further in that said transmitting means comprises an optical fiber having a light emitting terminus, said optical fiber extending from said light emitting terminus to a predetermined location on the oral airway, and a light emitting device operatively connected to said optical fiber for directing light to travel along said optical fiber.

7. The oral airway of claim 6 wherein said light emitting device comprises a light emitting diode.

* * * * *